United States Patent
Errico et al.

[11] Patent Number: 6,063,089
[45] Date of Patent: May 16, 2000

[54] SIDE MOUNTED POLYAXIAL PEDICLE SCREW

[75] Inventors: Joseph P. Errico, Far Hills; Thomas J. Errico, Summit; James D. Ralph, Oakland, all of N.J.

[73] Assignee: Spinal Concepts, Inc., Austin, Tex.

[21] Appl. No.: 09/059,162

[22] Filed: Apr. 13, 1998

Related U.S. Application Data

[63] Continuation of application No. 08/772,407, Dec. 23, 1996, Pat. No. 5,776,135.

[51] Int. Cl.[7] .................................................. A61B 17/70
[52] U.S. Cl. .......................... 606/61; 606/60; 606/72; 606/73
[58] Field of Search ................... 606/61, 60, 72, 606/73

[56] References Cited

U.S. PATENT DOCUMENTS

| | | |
|---|---|---|
| 5,306,307 | 4/1994 | Senter et al. . |
| 5,306,309 | 4/1994 | Wagner et al. . |
| 5,425,772 | 6/1995 | Brantigan . |
| 5,437,669 | 8/1995 | Yuan et al. . |
| 5,443,467 | 8/1995 | Biedermann et al. . |
| 5,474,551 | 12/1995 | Finn et al. . |
| 5,476,464 | 12/1995 | Metz-Stavenhagen et al. . |
| 5,540,688 | 7/1996 | Navas . |
| 5,569,246 | 10/1996 | Ojima et al. . |
| 5,584,831 | 12/1996 | McKay . |
| 5,609,635 | 3/1997 | Michelson . |
| 5,683,393 | 11/1997 | Ralph ........................................ 606/61 |
| 5,776,135 | 7/1998 | Errico et al. . |

FOREIGN PATENT DOCUMENTS

| | | |
|---|---|---|
| 97/38640 | 10/1997 | WIPO . |
| 98/12976 | 4/1998 | WIPO . |
| 98/14142 | 4/1998 | WIPO . |

*Primary Examiner*—Michael Buiz
*Assistant Examiner*—Julian W. Woo
*Attorney, Agent, or Firm*—Conley Rose & Tayon PC

[57] ABSTRACT

A polyaxial orthopedic device for use with rod implant apparatus which includes a screw having a head, a tubular body having holes in the top, side and bottom therof, and a rod coupling element. The head of the screw is disposed in the body with the shaft of the screw extending out the bottom hole, such that the body and the screw may initially rotate relative to one another. The rod coupling element has a ball shaped end which seats in the body with the remainder of the rod coupling element extending out of the side hole of the body, such that the rod coupling element and the body are initially polyaxially coupled relative to one another. The ball end of the rod coupling element is disposed on top of the head of the screw. A set screw is provided in the top of the body, the tightening of which causes the ball, head, and body to be crush locked together, thereby preventing further relative motion.

30 Claims, 3 Drawing Sheets

6,063,089

SIDE MOUNTED POLYAXIAL PEDICLE SCREW

This is a continuation of copending application Ser. No. 08/772,407 filed Dec. 23, 1996 now U.S. Pat. No. 5,776,135.

BACKGROUND OF THE INVENTION

1. Field of the Invention

This invention relates generally to a side mounted polyaxial pedicle screw apparatus for use with orthopedic fixation systems, and more particularly, to a screw for insertion into spinal bone, and a coupling element polyaxially mounted thereto for coupling the screw to an orthopedic implantation structure, such as a rod.

2. Description of the Prior Art

The spinal column is a highly complex system of bones and connective tissues which houses and protects critical elements of the nervous system and the arterial and veinous bodies in close proximity thereto. In spite of these complexities, the spine is a highly flexible structure, capable of a high degree of curvature and twist through a wide range of motion.

Genetic or developmental irregularities, trauma, chronic stress, tumors, and disease, however, can result in spinal pathologies which either limit this range of motion, or which threaten the critical elements of the nervous system housed within the spinal column. A variety of systems have been disclosed in the art which achieve this immobilization by implanting artificial assemblies in or on the spinal column. These assemblies may be classified as anterior, posterior, or lateral implants. As the classification suggests, lateral and anterior assemblies are coupled to the anterior portion of the spine, which is the sequence of vertebral bodies. Posterior implants are attached to the back of the spinal column, generally hooking under the lamina and entering into the central canal, attaching to the transverse process, or coupling through the pedicle bone. It would be desirable to have spinal fixation devices for immobilizing and altering the alignment of the spine over a large number, for example more than three or four, vertebra by means of affixing at least one elongate rod to the sequence of selected bones.

Such "rod assemblies" generally include a plurality of screws which are implanted through the posterior lateral surfaces of the laminae, through the pedicles, and into their respective vertebral bodies. The screws are provided with coupling elements, for receiving an elongate rod therethrough. The rod extends along the axis of the spine, coupling to the plurality of screws via their coupling elements. The aligning influence of the rod forces the spine to which it is affixed, to conform to a more proper shape.

It has been identified, however, that a considerable difficulty is associated with inserting screws along a misaligned curvature and simultaneously exactly positioning the coupling elements such that the receiving loci thereof are aligned so that the rod can be passed therethrough without distorting the screws. Attempts at achieving proper alignment with fixed screws is understood to require considerably longer operating time, which is known to increase the incidence of complications associated with surgery. Often such alignments, with such fixed axes devices could not be achieved, and the entire instrumentationing effort would end unsuccessfully.

In addition, for many patient's specific pathology it is desirable that the rod extend down into and beyond the lumbar portion of the spine, and for the end of the rod to be coupled to the sacral bone. Providing such an end to the assembly in the sacral bone has been understandably suggested inasmuch as it provides superior support to the full extent of the assembly. The most suitable position for the insertion of the screws into the sacral body may not, however, conform to the direction extent of the rod as it is affixed to the entirety of the assembly. Misalignment of the rod with respect to the screw and the coupling element is often a source of considerable disadvantage for the surgeon, often requiring considerable efforts to be expended bending and aligning the rod with the receiving locus of the coupling element. These additional efforts are a considerable difficulty associated with the proper and expeditious affixation, and over the long term, the offset of the rod can have a deleterious effect on the overall performance of the entire implantation assembly.

Further, it has been recognized that implant devices which must be positioned too high relative to the anatomically natural bone surface can cause continuous irritation to the soft tissues, i.e., muscles, nerves, blood vessels, skin, etc. It has therefore been a design goal for advanced pedicle screw systems to present as low a bone surface profile as is possible. Unfortunately, the goal has traditionally been one which runs counter to the goal of providing greater flexibility, i.e., polyaxialability, in pedicle screw devices.

The art contains a variety of attempts at providing instrumentation which permit a freedom with respect to angulation of the screw and the coupling element. These teachings, however, have generally been complex, and inadequately reliable with respect to durability. The considerable drawbacks associated with the prior art systems include complexity, difficulty properly positioning the rod and coupling elements, and the tedious manipulation of the many parts associated with the complex devices.

It is, therefore, desirable to provide a pedicle screw and coupling element assembly which provides a polyaxial freedom of implantation angulation with respect to rod reception.

In addition, it is desirable to provide such an assembly which comprises a reduced number of elements, and which correspondingly provides for expeditious implantation.

Accordingly it is also desirable to provide an assembly which is reliable, durable, and provides long term fixation support.

In addition, it is also desirable to provide an advanced polyaxial pedicle screw which presents a very low profile relative to the natural anatomical bone surface to limit long-term soft tissue irritation.

Other features not explicitly stated will be set forth and will be more clearly understood in conjunction with the descriptions of the preferred embodiments disclosed hereafter.

SUMMARY OF THE INVENTION

The preceding features are achieved by a polyaxial locking screw for use with rod stabilization and immobilization systems in the spine. More particularly, the polyaxial assembly includes a bone screw having a traditional threaded shaft portion, as well as a disc shaped head. The shaft may further include a slight annular recession formed in the exterior surface directly beneath the head.

In addition, the assembly includes a generally cylindrical body portion which has an open tubular conformation, with a threaded top opening and a narrowed bottom opening. The body further includes a single hole formed in the lower side thereof; the hole being bell-shaped insofar as a portion thereof is sufficiently large to permit the disc shaped head of the screw to enter laterally therethrough. The hole in the side of the body is connected to the hole in the bottom of the body by a channel which is as wide as the diameter of the shaft at the annularly recessed portion thereof. This permits the head to be inserted through the lateral hole in the body and then to seat in the bottom of the body with the shaft portion extending downwardly through the hole in the bottom. Therefore, the head is nested at the bottom of the body such that it seats loosely on the rim of the bottom opening, and such that the annular recessed portion of the shaft extends out of the bottom opening in the body, the body may rotate relative to the shaft to facilitate its proper positioning, but may not slide axially along the shaft.

The top hole in the body is threaded to receive a threaded set screw.

The rod coupling element includes a ball shaped portion formed at one end thereof, which is designed to nest within the body, on top of the disc shaped head of the shaft. An elongate intermediate portion of the rod coupling element extends out from the ball, through the lateral hole in the body, to form the rod coupling portion. In a preferred embodiment the rod coupling portion includes a hook-shaped end into which a rod may be locked by use of a second set screw. It shall be understood that the rod coupling portion may include a variety of alternative rod securing means, all being contemplated as potential variations.

In an embodiment of the above described rod coupling portion, i.e., the hook-shaped portion, a threaded bore is formed through a region of the elongate intermediate portion of the rod coupling element at a position which is adjacent to the hook shaped portion. This feature, which is briefly described hereinbelow, is more fully set forth in U.S. Pat. No. 5,683,393, entitled "Bidirectional Rod-Hook Locking Mechanism". In this preferred locking mechanism, the bore is sufficiently close to the hook shaped portion that the medial portion of the bore forms an opening into the central portion of the hook shaped surface. The radius of the hook shaped surface is designed to be substantially equivalent to the curvature of the rod which is to be received in the hook. The set screw includes an hourglass shaped locking shaft which is disposed in the bore, having threading provided on the upper and lower portions thereof. The axial curvature of the medial portion (i.e., the inwardly tapered portion) of the hourglass shaped locking shaft is substantially equivalent to the missing curvature of the surface of the hook shaped portion. Thus, when the locking shaft is disposed in the bore, such that the medial portion of the locking shaft is aligned properly relative to the opening in the surface of the hook shaped portion, a rod of proper size may be placed in the hook shaped portion. Once placed therein, however, rotational advance of the locking shaft in the bore causes an offset of the surfaces of the locking shaft and the hook shaped portion, such that an interference lock may be provided against the rod, thereby holding the rod in the hook shaped portion.

In order to facilitate the placement of the rod in the hook shaped portion, the ball end of the rod coupling element is permitted to rotate within the hole of the body prior to the locking down of the set screw which locks the ball end of the rod coupling element rigidly relative to the body. This locking operation on the set screw further causes the bottom rim of the bottom hole in the body to be lifted upwardly relative to the screw, thereby crush locking the bottom of the body to the undersurface of the disc-shaped head, thereby locking the body and ball relative to the shaft.

The first step in the process of implanting is to insert the shaft into the appropriate position in the spinal bone (i.e., the sacrum or the pedicle). The head of the shaft may be inserted through the side of the body either before implantation of the shaft, or after. (It shall be understood that the placement of the body on the shaft prior to implantation of the shaft may require the removal of the top set screw from the body such that the shaft may be driven into the bone by a suitable screwdriving instrument.)

Once the shaft is driven into the bone, and the body is placed on the head, the body is rotated into position to receive the ball of the rod coupling element therein. The ball is inserted into the body, through the lateral hole therein, such that it seats against the top surface of the head of the shaft. The ball may be polyaxially rotated through a range of angles relative to the body and shaft (in three dimensional range of motion—when the motion of the body is included), this range being solely limited by the relative sizes of the side opening in the body and the size of the intermediate portion of the rod coupling element. This freedom of positioning permits the hook shaped portion of the rod coupling element to be coupled to the rod more easily than in previous designs. (In the preferred embodiment, the rod is positioned in the hook-shaped portion and is then locked therein by the locking shaft as it is rotated to create an interference lock against the rod.)

Once the rod has been secured properly, the set screw in the top of the body is rotated downward within the body, thereby crushing the ball end of the rod coupling element to the top of the head of the screw, and drawing the rim portion of the hole in the bottom of the body into crush locking contact with the underside of the disc shaped head of the screw.

Multiple screw and coupling element assemblies are generally necessary to complete the full array of anchoring sites for the rod immobilization system, however, the screw and coupling element assembly is designed to be compatible with alternative rod systems so that, where necessary, it may be employed to rectify the failures of other systems the implantation of which may have already begun.

DETAILED DESCRIPTION OF THE PREFERRED EMBODIMENT

While the present invention will be described more fully hereinafter with reference to the accompanying drawings, in which particular embodiments and methods of implantation are shown, it is to be understood at the outset that persons skilled in the art may modify the invention herein described while achieving the same functions and results of this invention. Accordingly, the descriptions which follow are to be understood as illustrative and exemplary of specific structures, aspects and features within the broad scope of the present invention and not as limiting of such broad scope.

Figure 1:
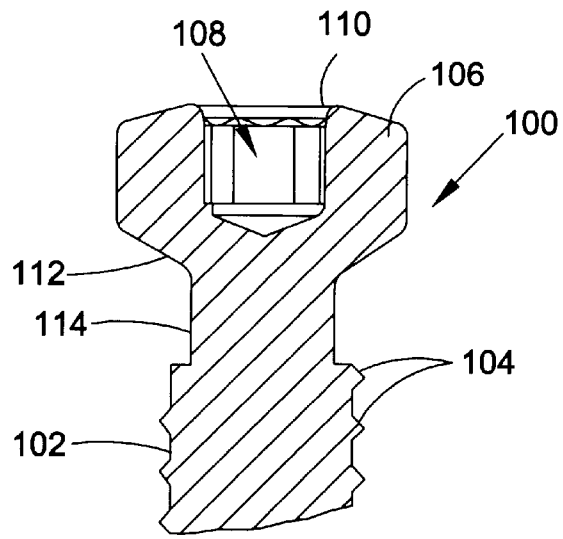
FIG. 1 is a side view of a screw.

Referring now to FIG. 1, a bone screw 100 is shown in a cross-section view. More particularly, the screw 100 includes a shaft portion 102 having a threading 104 provided thereon, this threading 104 being ideally suited for strong purchase strength. The screw 100 further includes a disc shaped head 106 which has a recess 108 formed therein for receiving a screwdriving tool. This recess 108 further includes an upper lip 110 which has been bored out to a curvate taper, this taper having a diametric radius of curvature which is constant. The disc shape of the head 106 further has a curvate taper 112 on the undersurface thereof, the purpose of which is to permit secure seating in the bottom of the body portion described more fully hereinbelow. Between the head 106 and the threaded shaft portion 102 is a slight annular recession 114 formed in the exterior surface of the screw.

Figure 2:
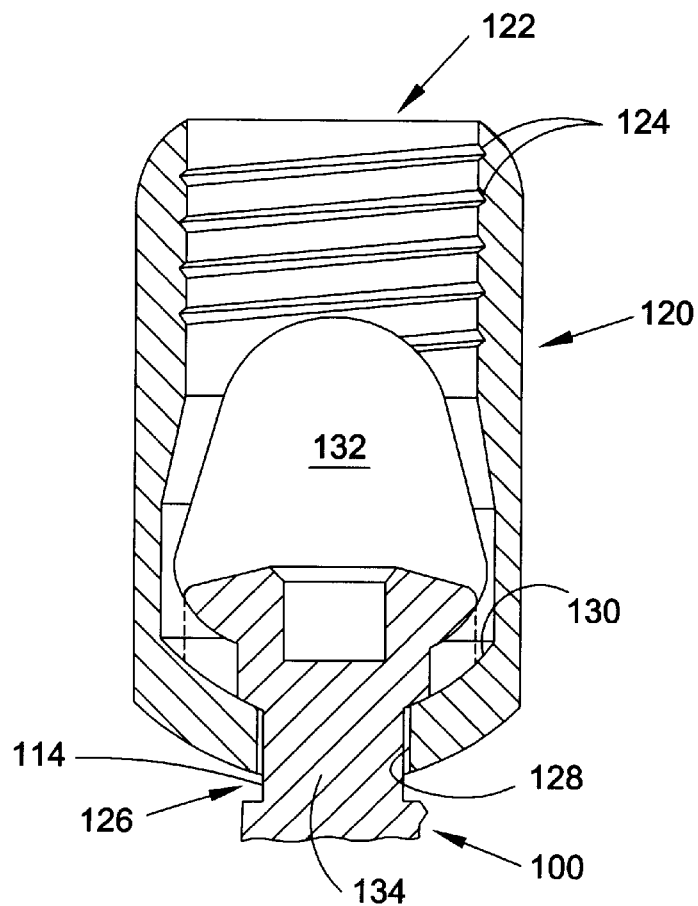
FIG. 2 is a side view of a body portion, disposed on the head of the shaft shown in FIG. 1.

Referring now to FIG. 2, the above-introduced body portion 120 is provided in a cross-section view wherein it is shown mounted to the head of the screw 100. The body 120 comprises a cylindrical element which has an open tubular conformation. It has an opening 122 in the top which includes a threading 124 for receiving a set screw (see FIG. 3 and appertaining discussion hereinbelow). In addition, the body 120 includes an opening 126 in the bottom thereof. This opening includes a lip 128 which has a curvate taper 130 which is substantially correspondingly shaped to the underside 112 of the head 106 of the screw 100 so as to permit secure nesting of the head 106 thereon.

The body 120 further includes a lateral hole 132 formed in side wall of the tube. This lateral hole 132 is bell-shaped insofar as the lower portion thereof is sufficiently large to permit the head 106 of the screw to enter laterally therethrough. The upper portion of the lateral hole 132 however is smaller so as to be ideally suited to receive the ball end of the rod coupling element (see FIG. 5 and the appertaining discussion.)

The lateral hole 132 in the side of the body is connected to the hole 126 in the bottom of the body by a channel 134 which is as wide as the diameter of the shaft of the screw at the annularly recessed portion 114 thereof. This channel permits the head 106 to be positioned in the body 120 through the lateral hole 132, and nest loosely at the bottom of the body (on the curvate surface 130 thereof) such that the annular recessed portion 114 and the shaft portion 102 extend out of the bottom opening 126 in the body. In this position, the body 120 and the screw 100 may rotate relative to one another, however, they may not translate axially relative to one another.

Figure 3:
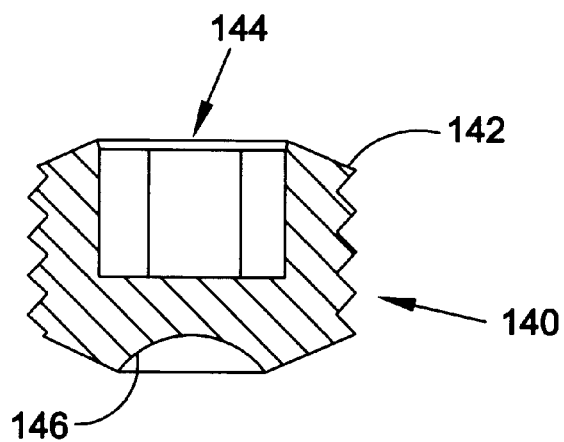
FIG. 3 is a side view of a set screw.

Referring now to FIG. 3, the set screw 140 is provided in a cross-section view. The set screw 140 includes a threading 142 which is suited to mate with the threading 124 of upper opening 122 in the body 120. The set screw 140 further includes a recess 144 formed therein which is provided so that a screwdriving instrument may be used to threadably advance it into the top opening 122. The set screw 140 also includes a concavely curved bottom surface 146, which surface is curved with a constant radius of curvature which is substantially equivalent to the radius of the ball portion of the rod coupling element (see FIG. 5 and appertaining discussion provided herein below.)

Figure 4:
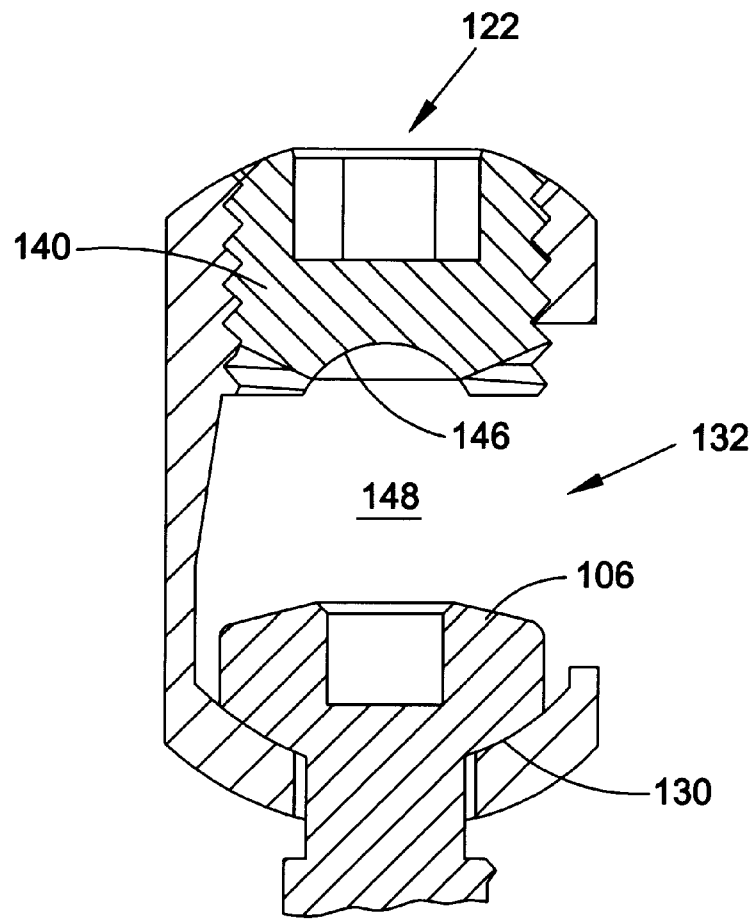
FIG. 4 is another side view of a body portion mounted on the head of the shaft shown in FIG. 1, wherein the direction of view is perpendicular to the plane of the view illustrated in FIG. 2, and wherein the set screw of FIG. 3 is disposed in the top of the body portion.

Referring now to FIG. 4, a side cross-section view of the screw 100, body 120, and set screw 140 assembly is provided. This view is taken along a plane which is rotated 90 degrees about the axis of the screw 100 as compared with the illustration provided in FIG. 2. This view demonstrates the nesting of the head 106 on the curved inner surface 130 of the bottom of the body 120. It also shows the set screw 140 having been advanced into the top opening 122. This view, therfore, illustrates the volume 148 positioned between the upper curved surface of the head 106 and the lower curved surface 146 of the set screw 140. This volume 148 is the space in which the ball end of the rod coupling element (see FIGS. 5 and 6 described hereinbelow) is retained.

Figure 5:
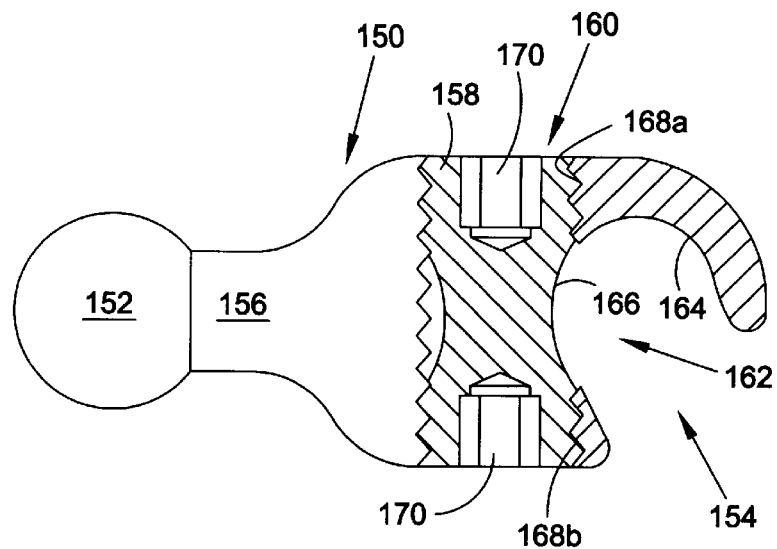
FIG. 5 is a side cross-section view of a rod coupling element invention.

Referring now to FIG. 5, a rod coupling element 150 is provided in a side cross-section view. The rod coupling element 150 comprises a ball shaped proximal end 152, and a rod coupling distal end 154. An intermediate portion 156 is provided in between the two ends. The ball 152 is designed to nest within the body volume 148 of the body 120, on top of the head 106 of the screw and beneath the set screw 140. This ball end 152 can polyaxially float in this volume prior to locking of the set screw 140 down onto the ball 152. Application of this locking force by downward advancement of the set screw 140 causes the ball 152 to be crushed between the head 106 and the bottom 146 of the set screw 140.

The intermediate portion 156 of the rod coupling element extends out from the ball 152 to the rod coupling distal end 154 through the lateral hole 132 of the body. The rod coupling distal end 154 may include many alternative means for selectively locking to a rod, however, the preferred embodiment described herein, and set forth more fully in a co-pending and previously mentioned U.S. Pat. No. 5,683,393, includes a hook-shaped conformation having a constant radius of curvature into which a rod may be locked by use of a threaded locking rod 158. The inner radius 164 of the hook-shaped end 154 is designed to be substantially equivalent to the curvature of a rod which is to be received and locked therein.

More specifically with respect to the locking means of this embodiment of the rod coupling element 150, a threaded bore 160 is formed in the intermediate portion 156 of the rod coupling element adjacent to the hook-shaped distal end 154. The bore 160 is sufficiently close to the hook-shaped portion that the medial portion of the bore 160 forms an opening 162 into the inner surface 164 of the hook-shaped end 154. The locking rod 158 is disposed in the bore 160. The locking rod 158 has an hourglass shape and a threading provided on its upper and lower portions 168a,168b, respectively. The axial curvature of the medial portion 166 (i.e., the inwardly tapered portion) of the hourglass shaped locking shaft 158 is substantially equivalent to the radius of curvature of the hook-shaped inner missing curvature of the inner surface of the hook-shaped end 154. Thus, when the locking rod 158 is disposed in the bore 160, such that the medial portion of the locking rod 158 is aligned properly relative to the opening 162 in the inner surface of the hook-shaped end 154, an orthopedic rod of proper size may be placed in the hook-shaped end 154. Once placed therein, however, upward advance of the locking rod 158 in the bore 160, via rotation of the rod 158 along the threading of the bore 160 causes an offset of the surfaces of the locking rod 158 and the inner surface 164 of the hook-shaped end 154, such that an interference lock may be provided against the rod, thereby holding the rod in the hook-shaped end. This locking rod 158 may be operationally accessed from either end thereof via recesses 170 formed in the ends thereof. This bidirectional access permits access to the locking means independent of the surgical preference of orientation of the hook-shaped end 154 relative to the rod, i.e., the rod being cradled or capped by the hook-shaped rod coupling end 154.

It shall be understood at the outset that this is one of a variety of potential rod coupling elements which may be utilized in conjunction with the present device, the critical features for use being a ball shaped proximal end 152 and a distal end 154 which can couple to a rod.

Figure 6:
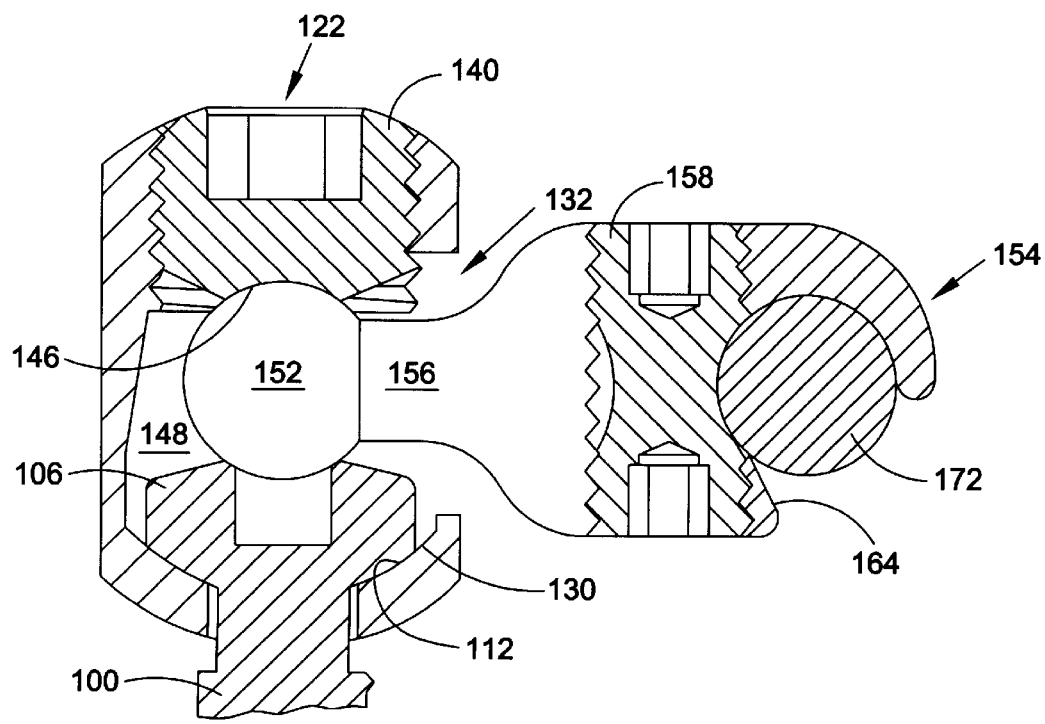
FIG. 6 is a side cross-section view of a fully assembled device.

Referring now to FIG. 6, the complete assembly of the preferred embodiment including an orthopedic rod 172 is provided in a cross-section view which is taken along the same plane as the view shown in FIG. 4. In order to facilitate the placement of the rod 172 in the hook-shaped end 154, the ball proximal end 152 of the rod coupling element 150 is permitted to float within the volume 148 of the body 120 prior to the locking down of the set screw 140. In addition the body 120 itself is able to rotate about the head 106 of the screw 100. The tightening of the set screw 140 into the top opening 122 of the body 120 causes the curved bottom rim 130 of the bottom hole 126 in the body 120 to be lifted upwardly relative to the screw 100, thereby crush locking it to the undersurface 112 of the disc-shaped head 106. This locks the body 120 relative to the screw 100 so that they cannot rotate relative to one another. In addition, the ball 152, set screw 140 and head 106 are locked together to prevent any further motion.

The first step in the process of implanting is to insert the shaft 102 of the screw 100 into the appropriate spinal bone (i.e., the sacrum or the pedicle). The head 106 of the screw 100 may be inserted through the lateral hole 132 of the body 120 and nested on the bottom surface 130 thereof either before implantation of the screw, or after. (It shall be understood that the placement of the body 120 on the head 106, prior to implantation, may require the removal of the set screw 140 from the body 120 so that the screw 100 may be driven into the bone by a screwdriving instrument—the recess 108 in the top of the screw 100 must be accessible.)

Once the screw 100 is driven into the bone, and the body 120 is placed on the head 106, the body 120 is rotated into position to receive the ball end 152 of the rod coupling element 150 through the lateral hole 132. The ball 152 is positioned in the body 120, such that it seats against the curved top surface 110 of the head 106. The ball 152 may be polyaxially rotated so that the rod coupling end 154 flows through a range of angles relative to the body 120 and head 106 (through an enlarged three dimensional range of motion relative to the screw when the rotational motion of the body 120 is also taken into account), this range being solely limited by the relative sizes of the lateral opening 132 in the body and the diameter of the intermediate portion 156 of the rod coupling element 150. This freedom of positioning permits the hook-shaped end 154 to be easily coupled to the rod 172. The rod 172 is positioned in the hook-shaped end 154 and locked therein by rotation of the locking rod 158 to interference lock the rod in place.

Once the rod 172 has been secured properly, the set screw 140 in the top opening 122 of the body 120 is rotated downward within the body 120, thereby crushing the ball end 152 of the rod coupling element 150 to the head 106 of the screw 100, and drawing the curved rim 130 of the bottom hole 126 into crush locking contact with the underside 112 of the disc shaped head 106 of the screw 100.

It shall be understood that if the diametric curvatures of the underside 112 of the head 106 and the inner lip 130 of the body 120 define a circle such that the circle defined by the diametric curvature of the upper lip 110 of the head 106 is concentric therewith, and the bottom opening 126 is larger than the recessed portion 114 of the shaft, but smaller than both the remainder of the shaft 102 and the head 106, then the body may polyaxially rotate on the head 106 as well as simply rotating. This additional flexibility may increase the surgical ease of use when implanting.

Multiple screw and coupling element assemblies are generally necessary to complete the full array of anchoring sites for the rod immobilization system, however, the screw and coupling element assembly is designed to be compatible with alternative rod systems so that, where necessary, if present invention may be employed to rectify the failures of other systems the implantation of which may have already begun.

While there has been described and illustrated embodiments of a polyaxial screw and coupling element assembly for use with posterior spinal rod implantation apparatus, it will be apparent to those skilled in the art that variations and modifications are possible without deviating from the broad scope. The present invention shall, therefore, be limited solely by the scope of the claims appended hereto.

We claim:

1. An orthopedic fixation system, comprising:
   a main body wherein the main body comprises:
   (a) a substantially cylindrical body defining an interior cavity;
   (b) a first opening into the interior cavity configured to hold a head of a bone screw within the main body and allow a shaft of the bone screw to extend from a coupling element and to rotate axially relative to the main body during use;
   (c) a second opening contiguous with the first opening and configured to allow the insertion of a bone screw head into the second opening and the simultaneous or subsequent insertion of the shaft of the same bone screw into the first opening; and
   (d) a third opening into the cavity configured to accommodate a locking mechanism;
   wherein the second opening is configured to accept a ball shaped end of a spinal rod coupling element and to allow rotation of the coupling element with respect to the main body, and further wherein the ball shaped end is positioned between a bone screw head and the locking mechanism during use such that the locking mechanism is effective to crush lock the ball shaped end against the screw head and to further crush lock the screw head against the main body when the locking mechanism is activated.

2. The orthopedic fixation system of claim 1, further comprising a bone screw, wherein the bone screw comprises a disc shaped head effective to mate with the outer surface of a ball shaped end of a rod coupling element.

3. The orthopedic fixation system of claim 1, further comprising a spinal rod coupling element comprising a first end configured to be coupled to a spinal rod, and a second end comprising a ball shape and an elongate intermediate portion connecting the first end to the second end.

4. The orthopedic fixation system of claim 3, wherein the spinal rod coupling element comprises a spinal rod locking mechanism effective to lock a spinal rod to the coupling element during use.

5. The orthopedic fixation system of claim 1, wherein the locking mechanism is a set screw.

6. An orthopedic fixation system, comprising:
   (i) a main body wherein the main body comprises:
   (a) a substantially cylindrical body defining an interior cavity;
   (b) a first opening into the interior cavity configured to hold a head of a bone screw within the main body and allow a shaft of the bone screw to extend from a coupling element and to rotate axially relative to the main body during use;

(c) second opening contiguous with the first opening and configured to allow the insertion of a bone screw head into the second opening and the simultaneous or subsequent insertion of the shaft of the same bone screw into the first opening; and (d) a third opening into the cavity configured to accommodate a locking mechanism;

(ii) a spinal rod coupling element comprising a first end configured to be coupled to a spinal rod, and a second end comprising a ball shape and an elongate intermediate portion connecting the first end to the second end; wherein the second opening is configured to accept a ball shaped end of the spinal rod coupling element and to allow rotation of the coupling element with respect to the main body, and further wherein the ball shaped end is positioned between a bone screw head and the locking mechanism during use such that the locking mechanism is effective to crush lock the ball shaped end against the screw head and to further crush lock the screw head against the main body when the locking mechanism is activated.

7. The orthopedic fixation system of claim 6, further comprising a bone screw, wherein the bone screw comprises a disc shaped head effective to mate with the outer surface of the ball shaped end of the rod coupling element.

8. The orthopedic fixation system of claim 6, wherein the spinal rod coupling element comprises a spinal rod locking mechanism effective to lock a spinal rod to the coupling element during use.

9. The orthopedic fixation system of claim 8, wherein the spinal rod locking mechanism comprises a locking rod and a substantially hook-shaped end, wherein a curvature of a medial portion of the locking rod is substantially equivalent to a radius of curvature of an inner surface of the substantially hook-shaped end.

10. The orthopedic fixation system of claim 6, wherein the locking mechanism is a set screw.

11. An orthopedic fixation system, comprising:
(i) a main body wherein the body comprises:
(a) a substantially cylindrical body defining an interior cavity;
(b) a first opening into the interior cavity configured to hold a head of a bone screw within the main body and allow a shaft of the bone screw to extend from a coupling element and to rotate axially relative to the main body during use;
(c) a second opening contiguous with the first opening and configured to allow the insertion of a bone screw head into the second opening and the simultaneous or subsequent insertion of the shaft of the same bone screw into the first opening; and
(d) a third opening into the cavity configured to accommodate a locking mechanism;
(ii) a spinal rod coupling element comprising a first end configured to be coupled to a spinal rod, and a second end comprising a ball shape and an elongate intermediate portion connecting the first end to the second end; and
(iii) a bone screw, wherein the bone screw comprises a disc shaped head effective to mate with the outer surface of the ball shaped end of the rod coupling element and a shaft;
wherein the second opening is configured to accept to the ball shaped end of the spinal rod coupling element and to allow rotation of the coupling element with respect to the main body, and further wherein the ball shape end is positioned between the bone screw head and the locking mechanism during use such that the locking mechanism is effective to crush lock the ball shaped end against the screw head and to further crush lock the screw head against the main body when the locking mechanism is activated.

12. The orthopedic fixation system of claim 11, wherein the bone screw further comprises an annular recession adjacent the screw head between the screw head and the shaft.

13. A method for coupling an orthopedic implantation structure to a spine, comprising:
inserting a bone screw into a spinal bone, the bone screw comprising a head and a shaft;
introducing the head of the bone screw into a body, wherein the body defines a first opening at a top of the body, a second opening in a side of the body, and a third opening formed in a bottom of the body, and wherein the body is configured to accept the head of the bone screw through the second opening and extend the shaft of the bone screw through the third opening wherein the head of the bone screw seats against the third opening;
rotating the body into position to receive a coupling element for coupling the orthopedic implantation structure, wherein the coupling element comprises a distal end and a proximal end, and wherein the distal end comprises a substantially hook-shaped portion, and wherein the proximal end is substantially ball-shaped;
placing the proximal end of the coupling element within the body, wherein the body is configured to allow the coupling element to substantially rotate polyaxially with respect to the bone screw;
positioning the orthopedic implantation structure in a desired configuration;
coupling the orthopedic implantation structure and the coupling element;
securing the orthopedic implantation structure within the distal end of the coupling element; and
inserting a set screw into the first opening of the body, and urging the set screw against a ball, wherein the set screw substantially fixes the proximal end of the coupling element within the body, and wherein the set screw substantially fixes the head of the bone screw within the body during use.

14. The method of claim 13, wherein introducing the head of the bone screw into the body comprises seating the bone screw against the bottom of the body, and wherein the body is configured to rotate with respect to the shaft.

15. The method of claim 13, wherein the distal end comprises a substantially hook-shaped portion, and wherein the coupling element comprises a bore for a locking rod, and wherein an opening is formed through a medial portion of the bore to an inner surface of the hook-shaped portion, and wherein rotating the locking rod within the bore secures the orthopedic implantation structure to the coupling element.

16. The method of claim 15, wherein the bore comprises threading on an inner portion thereof, and wherein the locking rod comprises threading on its upper and lower portions, and wherein the locking rod is substantially hourglass-shaped, and wherein the axial curvature of a medial portion of the locking rod is substantially similar to the curvature of an inner surface of the hook-shaped portion, and wherein the hook-shaped portion is configured to couple the orthopedic implantation structure, and wherein positioning the locking rod comprises rotating the locking rod such that an interference lock between the orthopedic implantation structure and the locking rod is formed.

17. A method of manufacturing an orthopedic fixation system, comprising:

providing a bone screw for insertion into a bone, the bone screw comprising a head and a shaft;

providing a coupling element for coupling the bone screw to an orthopedic implantation structure, the coupling element comprising a distal end and a proximal end, wherein the distal end is configured to secure the orthopedic implantation structure to the coupling element and the proximal end comprises a ball shape; and providing a body for securing the coupling element to the bone screw, wherein the body is configured to accept the head of the bone screw and the proximal end of the coupling element, and wherein the body is configured to allow the coupling element to rotate polyaxially with respect to the bone screw; and further wherein the body comprises a locking mechanism effective to crush lock the head of the screw and the ball shaped end of the coupling element in the body and prevent further rotation of the screw and the coupling element with respect to the body when the locking mechanism is activated.

18. The orthopedic fixation system of claim 3, wherein the first end of the spinal rod coupling element is substantially hook-shaped, and wherein the rod coupling element further comprises a set screw configured to contact a spinal rod disposed in the hook-shaped end during use.

19. The orthopedic fixation system of claim 18, wherein the hook-shaped end forms a substantially circular channel with an open portion, and wherein the set screw forms a portion of the circular channel.

20. The orthopedic fixation system of claim 18, wherein the elongate intermediate portion comprises a threaded bore, wherein a portion of the bore forms an opening in the circular channel.

21. The orthopedic fixation system of claim 20, wherein the threaded bore is open on both ends.

22. The orthopedic fixation system of claim 20, further comprising an hourglass-shaped threaded rod configured to be threadable in the threaded bore, and wherein the middle section of the threaded rod is configured to conform to the shape of a spinal rod disposed in the circular channel during use.

23. The orthopedic fixation system of claim 22, wherein the threaded rod is configured such that turning the threaded rod in either direction is effective to compression lock a spinal rod in the hook-shaped end during use.

24. The orthopedic fixation system of claim 3, wherein the spinal rod coupling element comprises;

a hook-shaped end that forms a substantially circular channel with an open portion for receiving a spinal rod and configured to fit the outer diameter of a spinal rod disposed therein;

a threaded bore in the elongate intermediate portion, wherein the bore is open on both ends, and wherein a portion of the bore forms an opening in the circular channel; and an hourglass-shaped threaded rod configured to be threadable in the threaded bore, wherein the middle section of the threaded rod is configured to conform to the shape of a spinal rod disposed in the circular channel, during use;

wherein turning the threaded rod in either direction in the threaded bore is effective to compression lock a spinal rod in the hook-shaped end during use.

25. A spinal rod coupling element comprising:

a first end configured to form a channel effective to connect to a spinal rod during use;

a second end configured to connect to a bone connecting device during use;

a connecting portion between the first end and the second end; and a threaded opening in the connecting portion proximate to the first end;

wherein the threaded opening is contiguous with an opening in a side of the first end so that a locking rod disposed in the opening contacts a spinal rod held in the first end during use.

26. The spinal rod coupling element of claim 25, wherein the threaded opening is open on both ends.

27. The spinal rod coupling element of claim 25, further comprising an hourglass-shaped locking rod configured to be threadable in the threaded opening.

28. The spinal rod coupling element of claim 27, wherein the hourglass-shaped locking rod comprises a middle portion, and wherein the middle portion is configured to conform to the curve of a spinal rod disposed in the first end during use.

29. The spinal rod coupling element of claim 27, wherein turning the locking rod in the threaded bore in either direction is effective to compression lock a spinal rod in the first end during use.

30. The spinal rod coupling element of claim 25, wherein the second end is ball shaped.

* * * * *

UNITED STATES PATENT AND TRADEMARK OFFICE
CERTIFICATE OF CORRECTION

PATENT NO. : 6,063,089
DATED : May 16, 2000
INVENTOR(S) : Joseph P. Errico, Thomas J. Errico and James D. Ralph It is certified that error appears in the above-indentified patent and that said Letters Patent is hereby corrected as shown below:

Claim 6, col. 9, line 1, please insert --a-- before the word "second".

Claim 11, col. 9, line 62, please delete "to" between the words "accept" and "the".

Signed and Sealed this

Twentieth Day of March, 2001

Attest:

NICHOLAS P. GODICI

*Attesting Officer*  *Acting Director of the United States Patent and Trademark Office*